(12) United States Patent
De La Torre

(10) Patent No.: US 9,427,419 B2
(45) Date of Patent: Aug. 30, 2016

(54) COMPOSITIONS COMPRISING DIMETHYL SULFOXIDE (DMSO)

(75) Inventor: Jack De La Torre, Gig Harbor, WA (US)

(73) Assignee: Abela Pharmaceuticals, Inc., Lake Forest, CA (US)

( * ) Notice: Subject to any disclaimer, the term of this patent is extended or adjusted under 35 U.S.C. 154(b) by 417 days.

(21) Appl. No.: 12/066,487

(22) PCT Filed: Sep. 11, 2006
(Under 37 CFR 1.47)

(86) PCT No.: PCT/US2006/035320
§ 371 (c)(1),
(2), (4) Date: Jan. 22, 2009

(87) PCT Pub. No.: WO2007/033082
PCT Pub. Date: Mar. 22, 2007

(65) Prior Publication Data
US 2009/0312273 A1    Dec. 17, 2009

Related U.S. Application Data

(60) Provisional application No. 60/716,335, filed on Sep. 12, 2005.

(51) Int. Cl.
*A61K 31/10* (2006.01)
*A61K 31/17* (2006.01)
*A61K 31/198* (2006.01)

(52) U.S. Cl.
CPC ............... *A61K 31/17* (2013.01); *A61K 31/10* (2013.01); *A61K 31/198* (2013.01)

(58) Field of Classification Search
None
See application file for complete search history.

(56) References Cited

U.S. PATENT DOCUMENTS

| | | |
|---|---|---|
| 3,334,012 A | 8/1967 | Herschler |
| 3,361,555 A | 1/1968 | Herschler |
| 3,393,080 A | 7/1968 | Erdi et al. |
| 3,419,619 A | 12/1968 | Soder et al. |
| 3,482,572 A | 12/1969 | Grosclaude et al. |
| 3,527,863 A | 9/1970 | Weichselbaum |
| 3,549,770 A | 12/1970 | Herschler et al. |
| 3,549,771 A | 12/1970 | Herschler |
| 3,551,554 A | 12/1970 | Herschler |
| 3,558,434 A | 1/1971 | Herschler |
| 3,573,214 A | 3/1971 | Kollonitsch |
| 3,592,936 A | 7/1971 | Marcus et al. |
| 3,654,165 A | 4/1972 | Bryant et al. |
| 3,675,654 A | 7/1972 | Baker et al. |
| 3,690,808 A | 9/1972 | St. Pierre |
| 3,711,606 A | 1/1973 | Herschler |
| 3,740,420 A | 6/1973 | Herschler et al. |
| 3,757,495 A | 9/1973 | Sievers |
| 3,773,838 A | 11/1973 | Andruski et al. |
| 3,790,682 A | 2/1974 | Herschler et al. |
| 3,823,676 A | 7/1974 | Cook et al. |
| 3,852,408 A | 12/1974 | Ewan et al. |
| 3,861,894 A | 1/1975 | Marsh |
| 3,881,003 A | 4/1975 | Rehm |
| 3,948,617 A | 4/1976 | Withorn |
| 3,972,962 A | 8/1976 | Williams et al. |
| 3,976,747 A | 8/1976 | Shale et al. |
| 3,988,129 A | 10/1976 | Fornoff et al. |
| 3,996,295 A | 12/1976 | Goeb |
| 4,015,025 A | 3/1977 | Szczesniak |
| 4,112,946 A | 9/1978 | Herschler |
| 4,125,589 A | 11/1978 | deVries |
| 4,129,122 A | 12/1978 | Dout et al. |
| 4,169,550 A | 10/1979 | Williams |
| 4,177,267 A | 12/1979 | Herschler |
| 4,194,628 A | 3/1980 | Campos |
| 4,202,676 A | 5/1980 | Pelosi, Jr. et al. |
| 4,212,392 A | 7/1980 | McKenzie |
| 4,225,381 A | 9/1980 | Ishikawa et al. |
| 4,252,054 A | 2/1981 | Bakels |
| 4,256,728 A | 3/1981 | Nishino et al. |
| 4,277,450 A | 7/1981 | Dilworth |
| 4,296,104 A * | 10/1981 | Herschler .................... 424/679 |
| 4,296,130 A | 10/1981 | Herschler |
| 4,307,067 A | 12/1981 | Tagawa et al. |
| 4,309,393 A | 1/1982 | Nguyen |
| 4,316,795 A | 2/1982 | Mooi |
| 4,333,922 A | 6/1982 | Herschler |
| 4,335,148 A | 6/1982 | Vidal et al. |

(Continued)

FOREIGN PATENT DOCUMENTS

| | | |
|---|---|---|
| CA | 2617934 | 2/2007 |
| EP | 0827744 | 3/1998 |

(Continued)

OTHER PUBLICATIONS

"Biological Effects of The Metabolites of Dimethyl Sulfoxide" by Kocsis et al., Ann. N.Y. Acad. Sci. 243, 104 09 (1975).*

"Arginine metabolism and the synthesis of nitric oxide in the nervous system," by Wiesinger, Progess in Neurobiology 64, 365-91 (2001).*

"In vitro induction of nitric oxide by fructose-1,6-diphosphate in the cardiovascular system of rats" by Rao et al., Mol. Cell. Biochem. 185, 171-75 (1998).*

"Medical use of dimethyl sulfoxide (DMSO)" by Swanson, Rev. Clin. Basic Pharm. 5, 1-33 (1985) (PubMed Abstract No. 3916302).*

(Continued)

*Primary Examiner* — Theodore R West
(74) *Attorney, Agent, or Firm* — Sheppard, Mullin, Richter & Hampton LLP

(57) ABSTRACT

The invention relates generally to compositions comprising dimethylsulfoxide (DMSO) and associated compounds in combination with one or more of the following: fructose 1,6-diphosphate, L-arginine, L-lysine, L-aspartate, and urea. Methods for treating traumatic brain injury, ischemic stroke, atherosclerosis, spinal cord trauma, and neurodegenerative illnesses are also provided.

24 Claims, 1 Drawing Sheet

(56) References Cited

U.S. PATENT DOCUMENTS

| | | |
|---|---|---|
| 4,341,675 A | 7/1982 | Nakamura |
| 4,350,245 A | 9/1982 | Elstner |
| 4,357,288 A | 11/1982 | Oas et al. |
| 4,369,190 A | 1/1983 | Schulte |
| 4,372,915 A | 2/1983 | Neti et al. |
| 4,413,109 A | 11/1983 | Haas |
| 4,424,330 A | 1/1984 | Raviola |
| 4,469,702 A | 9/1984 | Schulte |
| 4,477,469 A | 10/1984 | Herschler |
| 4,491,563 A | 1/1985 | Reusser et al. |
| 4,493,930 A | 1/1985 | Klayman et al. |
| 4,497,824 A | 2/1985 | Schulte |
| 4,505,708 A | 3/1985 | Gajewski et al. |
| 4,507,114 A | 3/1985 | Bohman et al. |
| 4,510,292 A | 4/1985 | Chiba et al. |
| 4,512,245 A | 4/1985 | Goldman |
| 4,514,421 A | 4/1985 | Herschler |
| 4,545,414 A | 10/1985 | Baum |
| 4,550,010 A | 10/1985 | Chelu |
| 4,559,329 A | 12/1985 | Herschler |
| 4,568,547 A | 2/1986 | Herschler |
| 4,575,515 A | 3/1986 | Sandborn |
| 4,591,497 A | 5/1986 | Naito et al. |
| 4,595,102 A | 6/1986 | Cianci et al. |
| 4,600,002 A | 7/1986 | Maryyanek et al. |
| 4,616,039 A | 10/1986 | Herschler |
| 4,616,064 A | 10/1986 | Zukosky et al. |
| 4,622,221 A | 11/1986 | Schleppnik |
| 4,626,530 A | 12/1986 | Schulte |
| 4,634,588 A | 1/1987 | Moroe |
| 4,642,177 A | 2/1987 | Mester et al. |
| 4,652,557 A | 3/1987 | Sandborn |
| 4,655,148 A | 4/1987 | Winship |
| 4,656,094 A | 4/1987 | Kojima et al. |
| 4,686,204 A | 8/1987 | Mester et al. |
| 4,710,353 A | 12/1987 | Tanaka et al. |
| 4,719,105 A | 1/1988 | Schleppnik |
| 4,721,813 A | 1/1988 | Mark et al. |
| 4,725,290 A | 2/1988 | Ohlmeyer et al. |
| 4,728,712 A | 3/1988 | Singh et al. |
| 4,729,835 A | 3/1988 | McNeillie et al. |
| 4,737,173 A | 4/1988 | Kudirka et al. |
| 4,747,845 A | 5/1988 | Korol |
| 4,751,241 A | 6/1988 | Motoyama et al. |
| 4,778,697 A | 10/1988 | Genske et al. |
| 4,784,909 A | 11/1988 | Emi et al. |
| 4,796,790 A | 1/1989 | Hamilton |
| 4,797,274 A | 1/1989 | Miki et al. |
| 4,803,047 A | 2/1989 | Pluim, Jr. |
| 4,830,718 A | 5/1989 | Stauffer |
| 4,834,721 A | 5/1989 | Onohara et al. |
| 4,850,268 A | 7/1989 | Saito et al. |
| 4,863,687 A | 9/1989 | Stevens et al. |
| 4,863,748 A | 9/1989 | Herschler |
| 4,887,751 A | 12/1989 | Lehman |
| 4,902,489 A | 2/1990 | Watanabe |
| 4,902,558 A | 2/1990 | Henriksen |
| 4,904,520 A | 2/1990 | Dumas et al. |
| 4,910,803 A | 3/1990 | Cukier |
| 4,911,691 A | 3/1990 | Aniuk et al. |
| 4,914,135 A | 4/1990 | Herschler |
| 4,916,767 A | 4/1990 | Uetake et al. |
| 4,919,925 A | 4/1990 | Ueda et al. |
| 4,931,276 A | 6/1990 | Franco et al. |
| 4,933,169 A | 6/1990 | Shanbrom |
| 4,937,115 A | 6/1990 | Leatherman |
| 4,940,405 A | 7/1990 | Kelly |
| 4,940,658 A | 7/1990 | Allen et al. |
| 4,941,991 A | 7/1990 | Rajamannan |
| 4,946,720 A | 8/1990 | Oishi et al. |
| 4,948,643 A | 8/1990 | Mueller |
| 4,948,787 A | 8/1990 | Chen et al. |
| 4,956,183 A | 9/1990 | Miki et al. |
| 4,973,605 A | 11/1990 | Herschler |
| 4,978,687 A | 12/1990 | Pascuchi |
| 4,980,045 A | 12/1990 | Krishna et al. |
| 4,988,505 A | 1/1991 | Watanabe et al. |
| 4,990,311 A | 2/1991 | Hirai et al. |
| 4,994,245 A | 2/1991 | Murray et al. |
| 5,001,794 A | 3/1991 | Uetake et al. |
| 5,006,510 A | 4/1991 | Ellis |
| 5,007,999 A | 4/1991 | Chin |
| 5,032,613 A | 7/1991 | Watson |
| 5,041,273 A | 8/1991 | Rock |
| 5,049,159 A | 9/1991 | Yamaji et al. |
| 5,049,163 A | 9/1991 | Huang et al. |
| 5,055,279 A | 10/1991 | Hirt et al. |
| 5,059,477 A | 10/1991 | Henriksen |
| 5,070,597 A | 12/1991 | Holt et al. |
| 5,071,622 A | 12/1991 | Dunson, Jr. |
| 5,071,686 A | 12/1991 | Genske et al. |
| 5,071,878 A | 12/1991 | Herschler |
| 5,083,558 A | 1/1992 | Thomas et al. |
| 5,086,804 A | 2/1992 | Ngai |
| 5,087,673 A | 2/1992 | Watanabe et al. |
| 5,091,180 A | 2/1992 | Walker et al. |
| 5,117,821 A | 6/1992 | White |
| 5,133,788 A | 7/1992 | Backus |
| 5,135,904 A | 8/1992 | Kamiya et al. |
| 5,139,831 A | 8/1992 | Mueller |
| 5,143,831 A | 9/1992 | Wong et al. |
| 5,145,657 A | 9/1992 | Kobayashi et al. |
| 5,149,576 A | 9/1992 | Potts et al. |
| 5,152,814 A | 10/1992 | Nelson |
| 5,160,707 A | 11/1992 | Murray et al. |
| 5,169,217 A | 12/1992 | Orchard et al. |
| 5,183,656 A | 2/1993 | Uesaka et al. |
| 5,190,640 A | 3/1993 | Roof et al. |
| 5,192,272 A | 3/1993 | Faure |
| 5,192,342 A | 3/1993 | Baron et al. |
| 5,192,498 A | 3/1993 | Chen et al. |
| 5,199,263 A | 4/1993 | Green et al. |
| 5,207,303 A | 5/1993 | Oswalt et al. |
| 5,213,680 A | 5/1993 | Kremer et al. |
| 5,218,036 A | 6/1993 | Kagawa et al. |
| 5,218,147 A | 6/1993 | Shaw |
| 5,240,478 A | 8/1993 | Messina |
| 5,260,090 A | 11/1993 | Isao |
| 5,269,294 A | 12/1993 | Rogozinski |
| 5,290,331 A | 3/1994 | Miles et al. |
| 5,335,373 A | 8/1994 | Dangman et al. |
| 5,336,431 A | 8/1994 | Richards et al. |
| 5,344,529 A | 9/1994 | Stauffer |
| 5,356,709 A | 10/1994 | Woo et al. |
| 5,358,443 A | 10/1994 | Mitchell et al. |
| 5,409,769 A | 4/1995 | Fukumoto et al. |
| 5,415,180 A | 5/1995 | Horan |
| 5,419,812 A | 5/1995 | Beal |
| 5,439,454 A | 8/1995 | Lo et al. |
| 5,441,729 A | 8/1995 | Salce et al. |
| 5,458,848 A | 10/1995 | Burgaud |
| 5,458,861 A | 10/1995 | Buchanan et al. |
| 5,460,625 A | 10/1995 | Johnson |
| 5,466,757 A | 11/1995 | Watanabe et al. |
| 5,480,860 A | 1/1996 | Dillon |
| 5,486,387 A | 1/1996 | Mueller |
| 5,487,766 A | 1/1996 | Vannier |
| 5,494,587 A | 2/1996 | Morlec et al. |
| 5,512,144 A | 4/1996 | Stauffer |
| 5,516,526 A * | 5/1996 | da la Torre ............ 424/449 |
| 5,521,268 A | 5/1996 | Ghyzel et al. |
| 5,531,987 A | 7/1996 | Bauer et al. |
| 5,538,545 A | 7/1996 | Dauber et al. |
| 5,562,127 A | 10/1996 | Fanselow et al. |
| 5,569,679 A | 10/1996 | Jacob |
| 5,578,540 A | 11/1996 | Banzi et al. |
| 5,582,865 A | 12/1996 | Rezuke et al. |
| 5,584,986 A | 12/1996 | Bartholic |
| 5,603,696 A | 2/1997 | Williams et al. |
| 5,605,635 A | 2/1997 | David |
| 5,607,647 A | 3/1997 | Kinkead |
| 5,616,408 A | 4/1997 | Oleszczuk et al. |
| 5,620,760 A | 4/1997 | Galimberti et al. |
| 5,624,649 A | 4/1997 | Gal |

(56) References Cited

U.S. PATENT DOCUMENTS

| | | |
|---|---|---|
| 5,626,820 A | 5/1997 | Rezuke et al. |
| 5,650,329 A | 7/1997 | Warner |
| 5,654,061 A | 8/1997 | Visioli |
| 5,658,801 A | 8/1997 | Poissant et al. |
| 5,667,799 A | 9/1997 | Caldwell et al. |
| 5,703,152 A | 12/1997 | Ohama |
| 5,712,044 A | 1/1998 | Fanselow et al. |
| 5,725,893 A | 3/1998 | Pittet et al. |
| 5,753,696 A | 5/1998 | Shealy et al. |
| 5,761,362 A | 6/1998 | Yang et al. |
| 5,779,679 A | 7/1998 | Shaw |
| 5,783,269 A | 7/1998 | Heilmann et al. |
| 5,789,046 A | 8/1998 | Mueller |
| 5,792,505 A | 8/1998 | Fulger et al. |
| 5,803,130 A | 9/1998 | Robben et al. |
| 5,803,249 A | 9/1998 | Harsanyi, Jr. et al. |
| 5,843,420 A | 12/1998 | Bauer et al. |
| 5,849,846 A | 12/1998 | Chen et al. |
| 5,861,096 A | 1/1999 | Mason et al. |
| 5,871,562 A | 2/1999 | Culoso |
| 5,885,566 A | 3/1999 | Goldberg |
| 5,891,508 A | 4/1999 | Barnum |
| 5,919,877 A | 7/1999 | Tanaglia |
| 5,928,744 A | 7/1999 | Heilmann et al. |
| 5,931,303 A | 8/1999 | Salvadori |
| 5,935,412 A | 8/1999 | Brainard, II |
| 5,935,547 A | 8/1999 | LeComte et al. |
| 5,948,398 A | 9/1999 | Hanamoto et al. |
| 5,958,502 A | 9/1999 | Fulger et al. |
| 5,965,276 A | 10/1999 | Shlenker et al. |
| 5,967,061 A | 10/1999 | Ashworth et al. |
| 5,972,993 A | 10/1999 | Ptchelintsev |
| 5,989,497 A | 11/1999 | Labonte, Jr. |
| 5,998,019 A | 12/1999 | Rosenbaum et al. |
| 6,007,520 A | 12/1999 | Sudo |
| 6,010,666 A | 1/2000 | Kurokawa et al. |
| 6,012,586 A | 1/2000 | Misra |
| 6,015,536 A | 1/2000 | Lokkesmoe et al. |
| 6,030,494 A | 2/2000 | Hupa et al. |
| 6,042,640 A | 3/2000 | Isganitis et al. |
| 6,045,596 A | 4/2000 | Holland, Jr. et al. |
| 6,048,733 A | 4/2000 | Machino et al. |
| 6,057,018 A | 5/2000 | Schmidt |
| 6,060,083 A | 5/2000 | Dorr et al. |
| 6,060,152 A | 5/2000 | Murchie |
| D427,299 S | 6/2000 | Haslebacher |
| 6,070,578 A | 6/2000 | Baughman et al. |
| 6,071,905 A | 6/2000 | Krasnov et al. |
| 6,077,335 A | 6/2000 | Schneider et al. |
| 6,090,076 A | 7/2000 | Lane, Jr. |
| 6,094,549 A | 7/2000 | Hiraoka et al. |
| 6,099,607 A | 8/2000 | Haslebacher |
| 6,106,502 A | 8/2000 | Richmond |
| 6,106,596 A | 8/2000 | Haramoto et al. |
| 6,110,176 A | 8/2000 | Shapira |
| 6,114,586 A | 9/2000 | Devaux et al. |
| D431,353 S | 10/2000 | Mellin |
| D431,902 S | 10/2000 | Mellin |
| 6,183,708 B1 | 2/2001 | Hei et al. |
| 6,183,758 B1 | 2/2001 | Scott |
| 6,197,288 B1 | 3/2001 | Mankoo |
| 6,207,106 B1 | 3/2001 | Kurokawa et al. |
| 6,221,325 B1 | 4/2001 | Brown et al. |
| 6,228,960 B1 | 5/2001 | Tanaglia |
| 6,238,767 B1 | 5/2001 | McCormack et al. |
| 6,248,733 B1 | 6/2001 | Landgrebe et al. |
| 6,261,655 B1 | 7/2001 | Rosenbaum et al. |
| 6,267,941 B1 | 7/2001 | Sata |
| 6,277,344 B1 | 8/2001 | Hei et al. |
| 6,294,161 B1 | 9/2001 | Hiramoto et al. |
| 6,303,200 B1 | 10/2001 | Woo et al. |
| 6,312,713 B1 | 11/2001 | Korol et al. |
| 6,318,075 B1 | 11/2001 | Gunther et al. |
| 6,348,177 B1 | 2/2002 | Bartley et al. |
| 6,349,826 B1 | 2/2002 | Kapik et al. |
| 6,365,099 B1 | 4/2002 | Castrantas et al. |
| 6,403,642 B1 | 6/2002 | Berg |
| 6,403,739 B1 | 6/2002 | Tanaglia et al. |
| 6,406,767 B1 | 6/2002 | Mueller |
| 6,412,639 B1 | 7/2002 | Hickey |
| 6,414,194 B1 | 7/2002 | Bloom, Jr. et al. |
| 6,416,772 B1 | 7/2002 | Van Engelen et al. |
| 6,418,932 B2 | 7/2002 | Paschal, Jr. et al. |
| 6,426,112 B1 | 7/2002 | Boatright |
| 6,426,370 B1 | 7/2002 | Hofschneider |
| 6,432,891 B1 | 8/2002 | O'Connor |
| 6,440,391 B1 | 8/2002 | Jacob |
| 6,454,097 B1 | 9/2002 | Blanco |
| 6,458,828 B1 | 10/2002 | Sakurai et al. |
| 6,460,702 B2 | 10/2002 | Hammond |
| 6,461,631 B1 | 10/2002 | Dunn et al. |
| 6,465,068 B1 | 10/2002 | Patel et al. |
| 6,468,259 B1 | 10/2002 | Loretti et al. |
| 6,475,466 B1 | 11/2002 | Ricci et al. |
| 6,479,150 B1 | 11/2002 | Liu et al. |
| 6,479,488 B1 | 11/2002 | Di-Fabio et al. |
| 6,482,377 B2 | 11/2002 | Bartley et al. |
| 6,495,096 B1 | 12/2002 | Hamaguchi et al. |
| 6,528,080 B2 | 3/2003 | Dunn et al. |
| 6,531,111 B1 | 3/2003 | Whalen, II et al. |
| 6,552,231 B2 | 4/2003 | Jones et al. |
| 6,562,447 B2 | 5/2003 | Wu et al. |
| 6,579,444 B2 | 6/2003 | Feimer et al. |
| 6,579,543 B1 | 6/2003 | McClung |
| 6,599,472 B1 | 7/2003 | Hudson |
| 6,620,911 B1 | 9/2003 | Pettit et al. |
| 6,632,842 B2 | 10/2003 | Chaudry et al. |
| 6,638,605 B1 | 10/2003 | Ankuda, Jr. et al. |
| 6,639,110 B2 | 10/2003 | Fremy |
| 6,649,193 B1 | 11/2003 | Colic |
| 6,652,845 B2 | 11/2003 | Hu et al. |
| 6,653,352 B2 | 11/2003 | Barr et al. |
| 6,656,723 B1 | 12/2003 | Phillips |
| 6,663,679 B1 | 12/2003 | Duncan |
| 6,680,194 B1 | 1/2004 | Turner |
| 6,706,257 B1 | 3/2004 | McCook et al. |
| 6,718,914 B2 | 4/2004 | Riddles |
| 6,722,295 B2 | 4/2004 | Zauderer |
| 6,723,349 B1 | 4/2004 | Hill et al. |
| 6,723,399 B2 | 4/2004 | Chundury et al. |
| 6,734,263 B2 | 5/2004 | Eadara et al. |
| 6,737,031 B2 | 5/2004 | Beal et al. |
| 6,737,089 B2 | 5/2004 | Wadsworth et al. |
| 6,743,523 B1 | 6/2004 | Woo et al. |
| 6,743,951 B2 | 6/2004 | Fremy |
| 6,761,169 B2 | 7/2004 | Eswarappa |
| 6,761,912 B2 | 7/2004 | Forusz et al. |
| 6,764,566 B1 | 7/2004 | Griesbach, III et al. |
| 6,783,004 B1 | 8/2004 | Rinner |
| RE38,597 E | 9/2004 | Lane, Jr. |
| 6,796,958 B2 | 9/2004 | Chen et al. |
| 6,797,042 B2 | 9/2004 | LaFerriere et al. |
| 6,822,015 B2 | 11/2004 | Muraki |
| 6,830,794 B2 | 12/2004 | Cartledge et al. |
| 6,844,430 B2 | 1/2005 | Pesce et al. |
| 6,846,535 B2 | 1/2005 | De Groot et al. |
| 6,858,192 B2 | 2/2005 | Graham et al. |
| 6,872,241 B2 | 3/2005 | Soane et al. |
| 6,881,419 B2 | 4/2005 | Lovett |
| 6,884,797 B2 | 4/2005 | Hofmann |
| 6,890,373 B2 | 5/2005 | Nemoto et al. |
| 6,902,714 B2 | 6/2005 | Skaarup Jensen et al. |
| 6,908,885 B2 | 6/2005 | Bengs et al. |
| 6,927,305 B2 | 8/2005 | Choudary et al. |
| 7,057,016 B2 | 6/2006 | Cerletti |
| 7,203,974 B2 | 4/2007 | Jones et al. |
| 7,282,224 B2 | 10/2007 | Roederer |
| 7,371,407 B2 | 5/2008 | Farmer |
| 7,381,521 B2 | 6/2008 | Whitaker |
| 7,955,418 B2 | 6/2011 | Claussen et al. |
| 8,298,320 B2 | 10/2012 | Cozean |
| 8,435,224 B2 | 5/2013 | Claussen et al. |
| 8,440,001 B2 | 5/2013 | Cozean |
| 8,480,797 B2 | 7/2013 | Cozean et al. |

(56) References Cited

U.S. PATENT DOCUMENTS

| | | |
|---|---|---|
| 8,673,061 B2 | 3/2014 | Cozean et al. |
| 2001/0005766 A1 | 6/2001 | Fremy |
| 2001/0047038 A1 | 11/2001 | Moorman et al. |
| 2002/0015762 A1 | 2/2002 | Quinlan |
| 2002/0025983 A1 | 2/2002 | Horrobin |
| 2002/0032131 A1 | 3/2002 | O'Connor |
| 2002/0043501 A1 | 4/2002 | Irvine |
| 2002/0090398 A1 | 7/2002 | Dunn et al. |
| 2002/0110549 A1 | 8/2002 | Till |
| 2002/0115729 A1 | 8/2002 | Yang |
| 2002/0131933 A1 | 9/2002 | Delmotte |
| 2002/0133100 A1 | 9/2002 | Paschal, Jr. et al. |
| 2002/0151753 A1 | 10/2002 | Fremy |
| 2002/0156326 A1 | 10/2002 | Fremy |
| 2002/0179647 A1 | 12/2002 | Hall et al. |
| 2002/0182263 A1 | 12/2002 | Stenti et al. |
| 2003/0017183 A1 | 1/2003 | Pollock |
| 2003/0032616 A1* | 2/2003 | Moskowitz et al. ............ 514/46 |
| 2003/0082321 A1 | 5/2003 | Kennedy et al. |
| 2003/0085170 A1 | 5/2003 | Scranton et al. |
| 2003/0108810 A1 | 6/2003 | Williamson et al. |
| 2003/0109495 A1 | 6/2003 | Kretschmer |
| 2003/0118672 A1 | 6/2003 | McPeak et al. |
| 2003/0133959 A1 | 7/2003 | Shacknai et al. |
| 2003/0149007 A1 | 8/2003 | Chaudry et al. |
| 2003/0152862 A1 | 8/2003 | Williamson et al. |
| 2003/0157006 A1 | 8/2003 | Hei et al. |
| 2003/0167033 A1 | 9/2003 | Chen et al. |
| 2003/0190266 A1 | 10/2003 | Tsurumi |
| 2003/0203009 A1 | 10/2003 | MacDonald |
| 2003/0203484 A1 | 10/2003 | Black et al. |
| 2004/0016410 A1 | 1/2004 | Riddles |
| 2004/0039066 A1 | 2/2004 | Crea |
| 2004/0048376 A1 | 3/2004 | Chabot et al. |
| 2004/0057972 A2 | 3/2004 | Shacknai et al. |
| 2004/0074212 A1 | 4/2004 | Yachi et al. |
| 2004/0081673 A1 | 4/2004 | Rayner et al. |
| 2004/0082667 A1 | 4/2004 | McCadden et al. |
| 2004/0086888 A1 | 5/2004 | Kornblith et al. |
| 2004/0087669 A1 | 5/2004 | Hausmanns et al. |
| 2004/0105943 A1 | 6/2004 | Hoerner et al. |
| 2004/0115818 A1 | 6/2004 | Puri et al. |
| 2004/0121023 A1 | 6/2004 | Stevens |
| 2004/0131806 A1 | 7/2004 | Barmore et al. |
| 2004/0137136 A1 | 7/2004 | Zheng et al. |
| 2004/0151826 A1 | 8/2004 | Milligan |
| 2004/0154220 A1 | 8/2004 | Holcomb |
| 2004/0156742 A1 | 8/2004 | Milan et al. |
| 2004/0157802 A1 | 8/2004 | Horwitz et al. |
| 2004/0186316 A1 | 9/2004 | Choudary et al. |
| 2004/0197339 A1 | 10/2004 | Brown |
| 2004/0213755 A1 | 10/2004 | Hochwalt et al. |
| 2004/0213774 A9 | 10/2004 | Till |
| 2004/0219126 A1 | 11/2004 | Seto et al. |
| 2004/0242818 A1 | 12/2004 | Williamson et al. |
| 2004/0265291 A1 | 12/2004 | Drake et al. |
| 2005/0025840 A1 | 2/2005 | Revnolds |
| 2005/0031651 A1 | 2/2005 | Gervais et al. |
| 2005/0031761 A1 | 2/2005 | Brucker et al. |
| 2005/0035062 A1 | 2/2005 | Hiltzik et al. |
| 2005/0054875 A1 | 3/2005 | Hei et al. |
| 2005/0058630 A1 | 3/2005 | Harris et al. |
| 2005/0069598 A1 | 3/2005 | Ribnicky et al. |
| 2005/0084412 A1 | 4/2005 | MacDonald et al. |
| 2005/0084438 A1 | 4/2005 | Do et al. |
| 2005/0084464 A1 | 4/2005 | McGrath et al. |
| 2005/0084474 A1 | 4/2005 | Wu et al. |
| 2005/0092070 A1 | 5/2005 | Bhatti |
| 2005/0092761 A1 | 5/2005 | Marganski et al. |
| 2005/0095653 A1 | 5/2005 | Goldstein et al. |
| 2005/0112085 A1 | 5/2005 | MacDonald et al. |
| 2005/0112176 A1 | 5/2005 | Dopson et al. |
| 2005/0112177 A1 | 5/2005 | Dopson et al. |
| 2005/0115895 A1 | 6/2005 | Simpson et al. |
| 2005/0136082 A1 | 6/2005 | Soane et al. |
| 2005/0136125 A1 | 6/2005 | Roth |
| 2005/0142096 A1 | 6/2005 | Wegner |
| 2005/0147692 A1 | 7/2005 | Roth |
| 2005/0158406 A1 | 7/2005 | McPeak et al. |
| 2005/0158424 A1 | 7/2005 | Nakano et al. |
| 2005/0169826 A1 | 8/2005 | Li |
| 2005/0176778 A1 | 8/2005 | Vermeer |
| 2005/0181048 A1 | 8/2005 | Romero |
| 2005/0182076 A1 | 8/2005 | Pacheco et al. |
| 2005/0187124 A1 | 8/2005 | Li et al. |
| 2005/0191343 A1 | 9/2005 | Liang |
| 2005/0215515 A1 | 9/2005 | Bucolo et al. |
| 2005/0222275 A1 | 10/2005 | Gabizon et al. |
| 2005/0224409 A1 | 10/2005 | Harshman et al. |
| 2005/0226827 A1 | 10/2005 | Ho |
| 2005/0227910 A1 | 10/2005 | Yang et al. |
| 2005/0260306 A1 | 11/2005 | Baldus |
| 2005/0261257 A1 | 11/2005 | Vermeer |
| 2005/0265979 A1 | 12/2005 | Aoki et al. |
| 2005/0266064 A1 | 12/2005 | McCarthy |
| 2005/0281883 A1 | 12/2005 | Daniloff et al. |
| 2006/0003069 A1 | 1/2006 | Zheng et al. |
| 2006/0006120 A1 | 1/2006 | Chen et al. |
| 2006/0006121 A1 | 1/2006 | Simpson et al. |
| 2006/0018933 A1 | 1/2006 | Vaya et al. |
| 2006/0018934 A1 | 1/2006 | Vaya et al. |
| 2006/0024365 A1 | 2/2006 | Vaya et al. |
| 2006/0052438 A1 | 3/2006 | Ho et al. |
| 2006/0121613 A1 | 6/2006 | Havens |
| 2006/0127508 A1 | 6/2006 | Larkins |
| 2006/0143767 A1 | 7/2006 | Yang et al. |
| 2006/0166948 A1 | 7/2006 | Vermeer |
| 2006/0177398 A1 | 8/2006 | McCook et al. |
| 2006/0194759 A1 | 8/2006 | Eidelson |
| 2006/0210646 A1 | 9/2006 | Oku et al. |
| 2006/0281822 A1 | 12/2006 | Appleton |
| 2007/0025950 A1 | 2/2007 | Elson |
| 2007/0028772 A1 | 2/2007 | Jain et al. |
| 2007/0048386 A1 | 3/2007 | Mallozzi, Sr. et al. |
| 2007/0180544 A1 | 8/2007 | Taylor et al. |
| 2007/0183936 A1 | 8/2007 | Newsam et al. |
| 2007/0243146 A1 | 10/2007 | Klock |
| 2007/0264212 A1 | 11/2007 | Ho |
| 2007/0270358 A1 | 11/2007 | Paoliambrosi |
| 2007/0292493 A1 | 12/2007 | Brierre |
| 2008/0038219 A1 | 2/2008 | Mosbaugh et al. |
| 2008/0076831 A1 | 3/2008 | Goetz |
| 2008/0102107 A1 | 5/2008 | Lewellyn et al. |
| 2008/0146458 A1 | 6/2008 | Hollingsworth et al. |
| 2008/0193427 A1 | 8/2008 | Kaesler et al. |
| 2008/0228161 A1 | 9/2008 | Claussen et al. |
| 2008/0249082 A1 | 10/2008 | Hollander |
| 2008/0251081 A1 | 10/2008 | Claussen et al. |
| 2008/0260871 A1 | 10/2008 | Fruitman |
| 2008/0274153 A1 | 11/2008 | Farmer |
| 2008/0275015 A1 | 11/2008 | Potter |
| 2008/0300311 A1 | 12/2008 | Kisak et al. |
| 2008/0317680 A1 | 12/2008 | Dueva-Koganov et al. |
| 2008/0319092 A1 | 12/2008 | Singh et al. |
| 2009/0215888 A1 | 8/2009 | Jagat et al. |
| 2009/0312273 A1 | 12/2009 | De la Torre |
| 2009/0324784 A1 | 12/2009 | Mclellan et al. |
| 2011/0105623 A1 | 5/2011 | Benjamin et al. |
| 2011/0136210 A1 | 6/2011 | Benjamin et al. |
| 2011/0203583 A1 | 8/2011 | Cozean et al. |
| 2011/0203585 A1 | 8/2011 | Cozean et al. |
| 2012/0207827 A1 | 8/2012 | Cozean et al. |
| 2013/0018059 A1 | 1/2013 | Jacob et al. |
| 2013/0045941 A1 | 2/2013 | Cozean et al. |
| 2014/0116444 A1 | 5/2014 | Cozean et al. |

FOREIGN PATENT DOCUMENTS

| | | |
|---|---|---|
| EP | 0976726 | 2/2000 |
| GB | 2 028 162 | 12/1979 |
| JP | 2003-306446 | 10/2003 |
| JP | 2005-0270589 | 10/2005 |
| JP | 2005330199 | 12/2005 |
| RU | 2035909 | 5/1995 |

(56) References Cited

FOREIGN PATENT DOCUMENTS

| | | |
|---|---|---|
| WO | WO 85/00108 | 1/1985 |
| WO | WO 94/05272 | 3/1994 |
| WO | WO 94/05273 | 3/1994 |
| WO | WO 9503753 A1 * | 2/1995 ............... A61F 2/02 |
| WO | WO 00/64868 | 11/2000 |
| WO | WO 01/73096 | 10/2001 |
| WO | WO 03/015760 | 2/2003 |
| WO | WO 03/101415 | 12/2003 |
| WO | WO 2004/064877 | 8/2004 |
| WO | WO 2004/067013 | 8/2004 |
| WO | WO 2004/093541 | 11/2004 |
| WO | WO 2004/100896 | 11/2004 |
| WO | WO 2005/054553 | 6/2005 |
| WO | WO 2005/115546 | 12/2005 |
| WO | WO 2005/117913 | 12/2005 |
| WO | WO 2006/129149 | 12/2006 |
| WO | WO 2006/135854 | 12/2006 |
| WO | WO 2007/009245 | 1/2007 |
| WO | WO 2007/016766 | 2/2007 |
| WO | WO 2007/033083 | 3/2007 |
| WO | WO 2007/033180 | 3/2007 |
| WO | WO 2007/049262 | 5/2007 |
| WO | WO 2007/056205 | 5/2007 |
| WO | WO 2007/098591 | 9/2007 |
| WO | WO 2007/126191 | 11/2007 |
| WO | WO 2008/049020 | 4/2008 |
| WO | WO 2008/091704 | 7/2008 |
| WO | WO 2008/098871 | 8/2008 |
| WO | WO 2010/054093 | 5/2010 |
| WO | WO 2010/062721 | 6/2010 |
| WO | WO 2011/053848 | 5/2011 |
| WO | WO 2011/053854 | 5/2011 |
| WO | WO 2011/123695 | 10/2011 |

OTHER PUBLICATIONS

Baer P, Thomas L, Shainhouse JZ. Treatment of osteoarthritis of the knee with a topical diclofenac solution: a randomized, controlled 6-week trial. BMC Musculoskeletal Disord. 2005; 6:44.
Cherian L, Robertson C. L-Arginine and Free Radical Scavengers Increase Cerebral Blood Flow and Brain Tissue Nitric Oxide Concentrations after Controlled Cortical Impact Injury in Rats. Journal of Neurotrauma, vol. 20, No. 1, (Jan. 2003), pp. 77-85.
Jacob et al., Interstitial Cystitis Network—Char Log, Topic: Understanding DMSO; Mar. 28, 2000; The IC Network.
Kubota et al. Beneficial effect of L-Arginine for Stroke-like episode in MELAS Brain and Development, Amsterdam, JL, vol. 26, No. 7, Oct. 1, 2004; pp. 481-483.
Pennsaid Monograph, Nuvo Research, 2010.
Robertson et al. "L-Arginine reduces neuronal damage after traumatic brain injury in the mouse" Journal of Neurotrauma, vol. 17, No. 10, Oct. 2000, p. 945.
Rosenbaum WM, Rosenbaum EE, Jacob S. The use of dimethyl sulfoxide (DMSO) for the treatment of intractable pain in surgical patients. Surgery 1965: 58, (Feb. 1965).
Roth SH, Shainouse JZ, Efficacy of Safety of a topical diclofenac solution (Pennsaid) in the treatment of primary osteoarthritis of the knee: a randomized, double-blind, controlled clinical trial. Arch Intern Med. Oct. 11, 2004;164(18):2017-23.
Shainhouse JZ, Grierson L, Naseer Z, A long-term, open-label study to confirm the safety of topical diclofenac solution containing dimethyl sulfoxide in the treatment of the osteoarthritic knee, American Journal of Therapeutics 0(0) 2010.
Shaklee Health Network, "Methyl Sulfonyl Methane," [online], 2006 [retrieved on Dec. 16, 2010]. Retrieved from the internet: <URL:http://content.hbiondemand.com/shap/monoVMN.asp?objID=100028]>: p. 1-4, especially p. 1, para 1 to p. 2, para 1.
Tugwell PS, Wells GA, Shainhouse JZ. Equivalence study of a topical diclofenac solution (Pennsaid) compared with oral diclofenac in symptomatic treatment of osteoarthritis of the knee: a randomized, controlled trial. J Rheumatol. Oct. 2004; 31(10):1893-5.
"Guidance on Medical Device Patient Labeling" accessed Mar. 10, 2010. http://www.fda.gov/MedicalDevices/DeviceRegulationandGuidance/GuidanceDocuments/ucm070782.htm.
Additive Free MSM Methylsulfonylmethane. World Image Naturals™, Inc. 2005. Downloaded from http://www.worldimagenaturals.com/products/msm/index.php. pp. 1-6.
AloeCalm™ All-Natural and Organic Body Lotion. Lanique Botanicals™. Downloaded from http://www.acne-answers.org/products/aloe-calm.html on Jul. 5, 2010. pp. 1-5.
Andrews, Jennifer M.: "Determination of minimum inhibitory concentrations," Journal of Antimicrobial Chemotherapy (2001) 48, Suppl. S1, 5-16.
Beilke, et al.: "Effects of dimethyl sulfoxide on the oxidative function of human neutrophils," (1987) Journal of Laboratory and Clinical Medicine 110:91-96.
Borodina, et al.: "Dimethylsulfone as a growth substrate for novel methylotrophic species of *Hyphomicrobium* and *Arthrobacter*," Arch Microbiol (2000) 173: 425-437.
Brandt, et al.: "Selective Affinity of Dimethyl Sulphoxide (DMSO) and 2-amino-4-phenylsulphonylbenzenesulphonamide (NSD 3004) for the Large Intestinal Mucosa of Mice," Acta pharmacol. Et toxicol. 1982, 51, 173-176.
Brown, Derek, F.J., et al.: "Guidelines for the laboratory diagnosis and susceptibility testing of methicillin-resistant *Staphylococcus aureus* (MRSA)," Journal of Antimicrobial Chemotherapy (2005) 56, 1000-1018.
Dancer, S. J.: "The effect of antibiotics on methicillin-resistant *Staphylococcus aureus*," Journal of Antimicrobial Chemotherapy (2008) 61, 246-253.
de Lencastre, et al.: "Antibiotic resistant *Staphylococcus aureus*: a paradigm of adaptive power," Curr Opin Microbiol. Oct. 2007; 10(5): 428-435.
Gerhards & Gibian, "The Metabolism of Dimethyl Sulfoxide and Its Metabolic Effect in Man and Animals," Annals New York Academy of Sciences, pp. 65-76, Mar. 1967.
Gupta, Shyam Dr.: "New Delivery System for Topical Nutraceutical (Nutracosmetic) and Cosmeceutical Formulations," pp. 1-5, Business Briefing: Global Cosmetics Manufacturing 2004.
Horváth, et al.: "Toxicity of methylsulfonylmethane in rats," Food and Chemical Toxicology 40 (2002) 1459-1462.
How to Flush the Toxins out of Your Body from the Swine or H1N1 Flu Shot, downloaded from http://www.ehow.com/print/how_5625054_flush-swine-hn-flu-shot.html, on Aug. 18, 2010. pp. 1-3.
Hucker, et al.: "Studies on the Absorption, Excretion and Metabolism of Dimethylsulfoxide (DMSO) in Man," The Journal of Pharmacology and Experimental Therapeutics, 155:309-317. 1967.
Jacob & Herschler: "Introductory Remarks: Dimethyl Sulfoxide After Twenty Years," Annals New York Academy of Sciences, Jun. 1983.
Layman, et al.: "The Absorption, Metabolism and Excretion of Dimethyl Sulfoxide by Rhesus Monkeys," Life Sciences, vol. 37, pp. 2431-2437, 1985.
Lee, et al.: "Evaluation of Genotoxicity on Plant-Derived Dietary Sulfar," J. Microbiol. Biotechnol. (2006), 16(5), 817-820.
Lu, et al.: "A Mouse Model for the Evaluation of Pathogenesis and Immunity to Influenza A (H5N1) Viruses Isolated from Humans," Journal of Virology, Jul. 1999, p. 5903-5911.
Magnuson, et al.: "Oral developmental toxicity study of methylsulfonylmethane in rats," Food and Chemical Toxicology 45 (2007) 977-984.
Magnuson, et al.: "Pharmacokinetics and Distribution of [$^{35}$S]Methylsulfonylmethane following Oral Administration to Rats," J. Agric. Food Chem. 2007, 55, 1033-1038.
Methylsulfonylmethane—Wikipedia, the free encyclopedia. Download from http://en.wikipedia.org/wiki/Methylsulfonylmethane, on Jul. 5, 2010. pp. 1-5.
MSM—MethylsulfonylMethane. Downloaded from http://pages.prodigy.net/naturedoctor/msm.html on Jul. 5, 2010. pp. 1-6.
Pratt, et al.: "A Study of the Absorption of OptiMSM (Methylsulfonylmethane) in Horses," Proceedings of the 17th Equine Nutrition and Physiology Society, 2001.

(56) References Cited

OTHER PUBLICATIONS

Scrubs, online encyclopedia article, accessed Mar. 10, 2010. http://en.wikipedia.org/wiki/Scrubs_(clothing).
Shanmugam, et al.: "The Effect of Methylsulfonylmethane on Hair Growth Promotion of Magnesium Ascorbyl Phosphate for the Treatment of Alopecia," Biomolecules & Therapeutics, 17(3), 241-248 (2009). ISSN 1976-9148.
Stürenburg, Enno: "Rapid detection of methicillin-resistant *Staphylococcus aureus* directly from clinical samples: methods, effectiveness and cost considerations," GMS German Medical Science 2009, vol. 7, ISSN 1612-3174. pp. 1-19.
Sulfur—MSM—methyl sulfonyl methane—Natural Health Site. A Basic Essential Nutrient Needed Now, More than Ever Before. Downloaded from http://www.all-natural.com/msm.html on Aug. 11, 2010. pp. 1-7.
Szmant, Harry H., "Physical Properties of Dimethyl Sulfoxide and Its Function in Biological Systems," Annals New York Academy of Sciences, pp. 20-23, Jan. 1975.
Tiews, et al.: "Metabolism and Excretion of Dimethyl Sulfoxide in Cows and Calves After Topical and Parenteral Application," Annals New York Academy of Sciences, pp. 139-150. Jan. 1975.
Vignes, Robert P., Ph.D: "Dimethyl Sulfoxide (DMSO): A Superior Solvent," Semiconductor Safety Association, Annual Meeting Apr. 25-28, 2000, Arlington, VA. pp. 1-47.
Williams, et al.: "Metabolism of Dimethyl Sulfide, Dimethyl Sulfoxide, and Dimethyl Sulfone in the Rabbit," Archives of Biochemistry and Biophysics 117, 84-87 (1966).
Windrum, et al.: "Variation in dimethyl sulfoxide use in stem cell transplantation: a survey of EBMT centres," Bone Marrow Transplantation (2005) 36, 601-603.
Wong, et al.: "Absorption, Excretion, and Biotransformation of Dimethyl Sulfoxide in Man and Minature Pigs After Topical Applicaton as an 80% Gel," The Journal of Investigative Dermatology, vol. 56, No. 1, 1971.
Zhang, et al.: "Assessment of methysulfonylmethane as a permeability enhancer for regional EDTA chelation therapy," infoma healthcare, Drug Delivery, 2009, 16(5): 243-248.
Adam, JB, Summary of Biomedical Treatments for Autism, ARI Publication 40, Apr. 2007.
Cárdenas, et al., "Fructose-1,6-bisphosphate inhibits the expression of inducible nitric oxide synthase caused by oxygen-glucose deprivation through the inhibition of glutamate related in rat forebrain slices", Arch. of Pharmacol., vol. 362(3):208-121 (2000).
Database WPI, Week 199604, Thomson Scientific, (May 1995).
Khazina et al., Tuberculostatic effect of the combined use of isoniazid and streptomycin with 5-fluorouracil in vitro, Problemy Tuberkuleza, Medicina, Moscow, Russia, vol. 58 (1): 63-66 (1980).
Life Extension Magazine, Sep. 1999 "The Multi-Purpose Compound MSM".
Ramirez, et al., DMSO in the Treatment of Mental Patients, Annals of the NY Acad. of Sci., vol. 141: 655-667 (1967).
Yang, TR, Gas Separation by Adsorption Process, Imperial College Press, 1987 pp. 11-12.
Web page entitled "fructose-1,6-diphosphate—Compound Summary", retrieved from the Internet Aug. 20, 2013, http://pubchem.ncbi.nlm.nih.gov/summary/summary.cgi?cid=10267&loc=ec_rcs.
Jacob, Web page entitled DMSO Dimethyl Sulfoxide; www.dmso.org; retrieved from the internet on Mar. 25, 2010.
Jacob, Web page entitled Dr. Jacob's Quality Assurance, www.jacoblab.com; as published on the Internet on Sep. 8, 2004.
Jacob, Web page Dr. Jacob's Quality Assurance, Natural Healthcare Solutions; www.jacoblab.com; retrieved from Internet on Mar. 25, 2010.
Ruslami et al., Pharmacokinetics and Tolerability of a Higher Rifampin Dose Versus the Standard Dose in Pulmonary Tuberculosis Patients, Antimicrobial Agents and Chemotherapy, vol. 51(7):2546-2551 (2007).
Aleksevich Ial, Piletskaia IG, Nikonorova VP. *Increase in the sensitivity of the microflora of pathological gingival pockets to streptomycin under the influence of dimexide and trypsin*. Mikrobiol Zh. Nov.-Dec. 1973; 35(6):766-9.
Barrager et al., *A Multicentered, Open-Label Trial on the Safety and Efficacy of Methylsulfonylmethane in the Treatment of Seasonal Allergic Rhinitis*, The Journal of Alternative and Complementary Medicine, vol. 8, No. 2, 2002, pp. 167-173.
Berry et al. *Natural Gas Odorants Desulfurization*, (2004) AIChE Annual National Meeting, Austin, Texas, Nov. 7-12.
Blumenthal L, Fuchs M. *The Clinical Use of Dimethyl Sulfoxide on Various Headaches, Musculoskeletal and Other General Medical Disorders*. Annals New York Academy of Sciences 1967:572-585.
Bookman A, Williams S, Shainhouse J. *Effect of a topical diclofenac solution for relieving symptoms of primary osteoarthritis of the knee: a randomized controlled trial*. CMAJ Aug. 17, 2004; 171(4):333-338.
Brayton CF. *Dimethyl Sulfoxide (DMSO); A Review*. The Cornel Veterinarian. Jan. 1986; 76(1):61-90.
Brechner V, Cohen D, Pretsky I. *Dermal Anesthesia by the Topical Application of Tetracaine Base Dissolved in Dimethyl Sulfoxide*, Annals New York Academy of Sciences. 1967:524-531.
Brien et al. *Systematic review of the nutritional supplements dimethyl sulfoxide (DMSO) and methylsulfonylmethane (MSM) in the treatment of osteoarthritis*. Osteoarthritis and Cartilage (2008) 16:1277-1288.
Brien S, Prescott P, Lewith G. *Meta-analysis of the Related Nutritional Supplements Dimethyl Sulfoxide and Methylsulfonlymethane in the Treatment of Osteoarthritis of the Knee*. eCAM Advance Access published May 27, 2009 in 10 pages.
Brown JH. *Clinical Experience with Dmso in Acute Musculoskeletal Conditions, Comparing a Noncontrolled Series with a Controlled Double Blind Study*. Ann NY Acad Sci 1967; 141(1):496-505.
Debi R, et al. *The Role of MSM in Knee Osteoarthritis: A Double Blind, RandomizedProspective Study*. Osteoarthritis and Cartilage (2008) 15 Supplemental C:C231 (426).
Demos C et al. *Dimethyl Sulfoxide in Musculoskeletal Disorders*. Ann NY Acad Sci 1967:517-523.
Eberhardt et al. *DMSO in patients with Active Gonarthrosis. A double-blind, placebo-controlled Phase III Study*. Fortschr Med, Nov. 10, 1995: 113(31):446-450.
Evans MS, Reid KH, Sharp JB. *Dimethylsulfoxide (DMSO) blocks conduction in peripheral nerve C fibers: a possible mechanism of analgesia*. Neuroscience Letters, 150 (1993):145-148.
Feldman WE, Punch JD, Holden PC. *In vivo and in vitro effects of dimethyl sulfoxide on streptomycin-sensitive and—resistant Escherichia coli*. Ann NY Acad Sci, Jan. 27, 1975; 243:269-77.
Florain, The Solid State Structures of the Dimethylformamide and Dimethylsulfoxide Complexes of Dioxodichloromolybdenum (VI), ProQuest, 30-07B (1969), pp. 66.
Glasser D. *Dimethylsulfoxide (DMSO) "resensibilization" as potential chemotherapy for opportunistic mycobacterial disease*. Am Rev Respir Dis. Nov. 1978; 118(5):969-70.
Gorbach IN, Samtsov VS. *Therapeutic possibilities of inhalation of rifampicin with dimexide in phthisiopulmonology*. Probl Tuberk. 1991; (3):34-6.
Haigler HJ et al. *Comparison of the Analgesic Effects of Dimethyl Sulfoxide and Morphine*, Ann NY Acad Sci 1983; (411):19-27.
Hasegawa T, *Suppressive Effects of Methylsulfonylmethane (MSM) on Type II Collagen-induced Arthritis in DBA/1J Mice*. Jpn Pharmacol Ther 2004; 32 (7):421-427.
Jacob S, Appleton J. *MSM: The Definitive Guide*—Chapter 6, 45-54, Part II, Chapter 7, 57-68, Chapter 8, 69-76, Chapter 10, 84-90, Chapter 21, 181-186. California: Freedom Press, 2003.
Jacob S, Lawrence R, Zucker M, *The Miracle of MSM—The Natural Solution for Pain*. New York: Library of Congress Cataloging-in-Publication Data, 1999.
Jacob SW, Herschler R. *Pharmacology of DMSO*, Cryobiology, 1985, 23(1):14-27.
Jacob, S.W. and Wood, D.C. *Dimethyl sulfoxide (DMSO): Toxicology, pharmacology, and clinical experience*. Am. J. Surg. 1967; 114(3):414-426.
Jagannath C, Reddy VM, Gangadharam PR. *Enhancement of drug susceptibility of multi-drug resistant strains of Mycobacterium*

(56) References Cited

OTHER PUBLICATIONS

*tuberculosis by ethambutol and dimethyl sulphoxide.* J Antimicrob Chemother. Mar. 1995; 35(3):381-90.

Jimenez RA, Willkens RF. *Dimethyl Sulphoxide: a perspective of its use in rheumatic diseases.* J Lab Clin Med 1982; 100(4):489-500.

John, H., Laudahn, G. *Clinical Experiences with the Topical Application of DMSO in Orthopedic Diseases: Evaluation of 4,180 Cases*, Annals New York Academy of Sciences, 1967; vol. 141:506-516.

Karlson AG, Ulrich JA, *Stock solutions of rifampin remain stable in dimethylsulfoxide for at least 8 months*, Appl Microbiol. Oct. 1969; 18(4):692-3.

Kim, et al. *Efficacy of Methylsulfonylmethane (MSM) in Osteoarthritis Path of the Knee: A Pilot Clinical Trial.* Osteoarthritis and Cartilage (2006) 14:286-294.

Knowles R. *Clinical Experience with DMSO in Small Animal Practice*, Annals New York Academy Sciences (1967) 141:478-483.

Koenen NJ, Haag RF, BiaP, RoseP. *Perkutane therapie bei aktivierter Gonarthrose.* Munch Med Wochenschr 1996; 138 (31-32):534-538.

Liubinets VI, Kruk MV. *Dimexide in the treatment of endobronchitis in patients with destructive forms of pulmonary tuberculosis*, Zh Ushn Nos Gorl Bolezn. Nov.-Dec. 1969; 29(6):68-71.

Lockie and Norcross. *A Clinical Study on the Effects of Dimethyl Sulfoxide in 103 Patients with Acute and Chronic Musculoskeletal Injuries and Inflammations*, Annals New York Academy Sciences (1967) 141:599-602.

Martin D. and Hauthal H., *Dimethyl Sulfoxide—Chapter 12.* New York: John Wiley & Sons, 1971.

Matsumoto, J. *Clincal Trials of Dimethyl Sulfoxide in Rheumatoid Arthritis Patients in Japan*, Annals New York Academy Sciences. 1967; vol. 141:560-568.

Mitinskaia LA, Iukhimenko NV, Kamaeva VF. *BCG vaccination and increasing the effectiveness of treatment of post-vaccination complications by the use of rifampicin and dimexide.* Probl Tuberk. 1994; (5):4-7.

Mohamaddi F, O'Mara K, Unusual Patient Odor Interfering with Care, Resurrection Medical Center, Chicago, Ill.

Muller U, Urbanczik R. *Influence of dimethyl sulfoxide (DMSO) on restoring sensitivity of mycobacterial strains resistant to chemotherapeutic compounds*, J Antimicrob Chemother. May 1979; 5(3):326-7.

Murav'ev IuV, Venikova MS, Peskovskaia GN, Riazantseva TA, Sigldin IaA. *Effect of dimethylsulphoxide and dimethyl sulfone.* Patol Fiziol Eksp Ter Mar.-Apr. 1991; (2):37-39.

Nash DR, Steingrube VA. *In vitro drug sensitivity of M. avium-intracellulare complex in the presence and absence of dimethyl sulfoxide.* Microbios. 1982; 35(140):71-8.

Oshima Y, Theodosakis J, Amiel D. *The Effect of Distilled Methylsulfonylmethane (MSM) on Human Chondrocytes in vitro.* World Congress on Osteoarthritis, Ft. Lauderdale, Florida; Osteoarthritis and Cartilage 2007; vol. 15 Supplemental C123:213.

Ostojic et. al. *Laboratory Testing of Cabin Air Filters for the Removal of Reduced-Sulfur Odors.* New Engine Design and Automotive Filtration SAE Special Publications 1998; 1362:41-58.

Paul M. *Interval Therapy with Dimethyl Sulfoxide.* Ann NY Acad Sci Mar. 1967; 1(141):586-598.

Paulus E. *FDA advisory committee meeting: methotrexate; guidelines for the clinical evaluation of anti-inflammatory drugs; DMSO in scleroderma.* Arthritis & Rehumatism Oct. 1986; 10(29):1289-1290.

Penrod, D., Bacharach, B., Templeton, J. *Dimethyl Sulfoxide for Incisional Path after Thoracotomy: Preliminary Report.* Annals New York Academy Sciences Mar. 15, 1967; vol. 141(1):493-495.

Pottz GE, Rampey JH, Bejamin F. *The effect of dimethyl sulfoxide (DMSO) on antibiotic sensitivity of a group of medically important microorganisms: preliminary report.* Ann NY Acad Sci. Mar. 15, 1967; 141(1):261-72.

Ropek M, Pawlowska I, Szydlowska T. *Effects of dimethyl sulfoxide on tubercle bacilli resistant to INH.* Gruzlica. Aug. 1971; 39(8):738-41.

Seibert F, Farrelly F, Shepherd C. *DMSO and other combatants against bacteria isolated from leukemia and cancer patients.* Ann NY Acad Sci Mar. 1967; 1(141):175-201.

Simon L, et. al. *Efficacy and Safety of Topical Diclofenac containing Dimethyl Sulfoxide (DMSO) compared with those of Topical Placebo, DMSO Vehicle and Oral Diclofenac for Knee Osteoarthritis.* Pain, 143(2009):238-245.

Smith G, Bertone AL, Kaeding C, et al. *Anti-Inflammatory effects of topically applied dimethyl sulphoxide gel on endotoxin-induced synovitis in horses.* Am J Vet Res Sep. 1998; 59(9):1149-52.

Steinberg, A. *The employment of DMSO as an anti-inflammatory agent and steroid transporter in diversified clinical diseases.* Ann NY Acad Sci 1967, 141(1):532-550.

Szydlowska T. *In Vitro and In Vivo Studies on the role of Dimethylsulfoxide (DMSO) in Resensibilization of Bacterial Strains Resistant to Antibiotics and Chemotherapeutic Agents.* Zbl. Bakt. Hyg., I. Abt. Orig. A 239, 270-274 (1977).

Szydlowska T, Pawlowska I. *Comparative Studies on the Influence of Dimethylsulfoxide (DMSO) on Reversion to Sensitivity to Isonicotinic Acid Hydrazide (INH) and Rifampicin (RMP) in Resistant Strains of Tubercle Bacilli.* Arch Immunol Ther Exp (Warsz). 1976; 24(4):575-77.

Szydlowska T, Pawlowska I. *In vivo studies on reversion to sensitivity of INH-resistant tubercle bacilli under the influence of dimethylsulfoxide (DMSO).* Arch Immunol Ther Exp (Warsz). 1974; 22(4):559-61.

Szydlowska T. *Studies on the role of dimethylsulfoxide in resensibilization of antibiotic-resistant bacterial strains.* Arch Immunol Ther Exp (Warsz). 1972; 20(2):193-202.

Szydlowska T. *Studies on the role of dimethylsulfoxide in resensibilization of bacterial strains resistant to sulfonamides.* Arch Immunol Ther Exp (Warsz). 1972; 20(2):203-207.

Teigland MB, Saurino V. *Clinical Evaluation of Dimethyl Sulfoxide in Equine Applications.* Ann NY Acad Sci Mar. 1967; 141(1):471-7.

Usha PR, Naidu MUR. *Randomized, double-blind, parallel, placebo-controlled study of oral glucosamine, methylsulfonylmethane and their combination in osteoarthritis.* Clin Drug Invest 2004; 24(6):353-63.

Vuopala U, et. al. *The Analgesic action of DMSO ointment in arthrosis.* Acta Rheum Scand 1971; 17(1):57-60.

Wierzbicki. *Homocysteine and cardiovascular disease: a review of the evidence*; Diabetes and Vascular Disease Research; Jun. 2007; pp. 143-149; vol. 4, Iss 2; The British Library.

Wood, DC, Wood, J. *Pharmacologic and Biochemical Considerations of Dimethyl Sulfoxide.* Ann NY Acad Sci Jan. 1975; 243:7-19.

Zuckner, J. Uddin, J., Gantner, G. *Local Application of Dimethyl Sulfoxide and DMSO Combined with Triamcinolone Acetonide in Rheumatoid Arthritis.* Ann NY Acad. Sci. Mar. 1967; 1(141):555-9.

\* cited by examiner

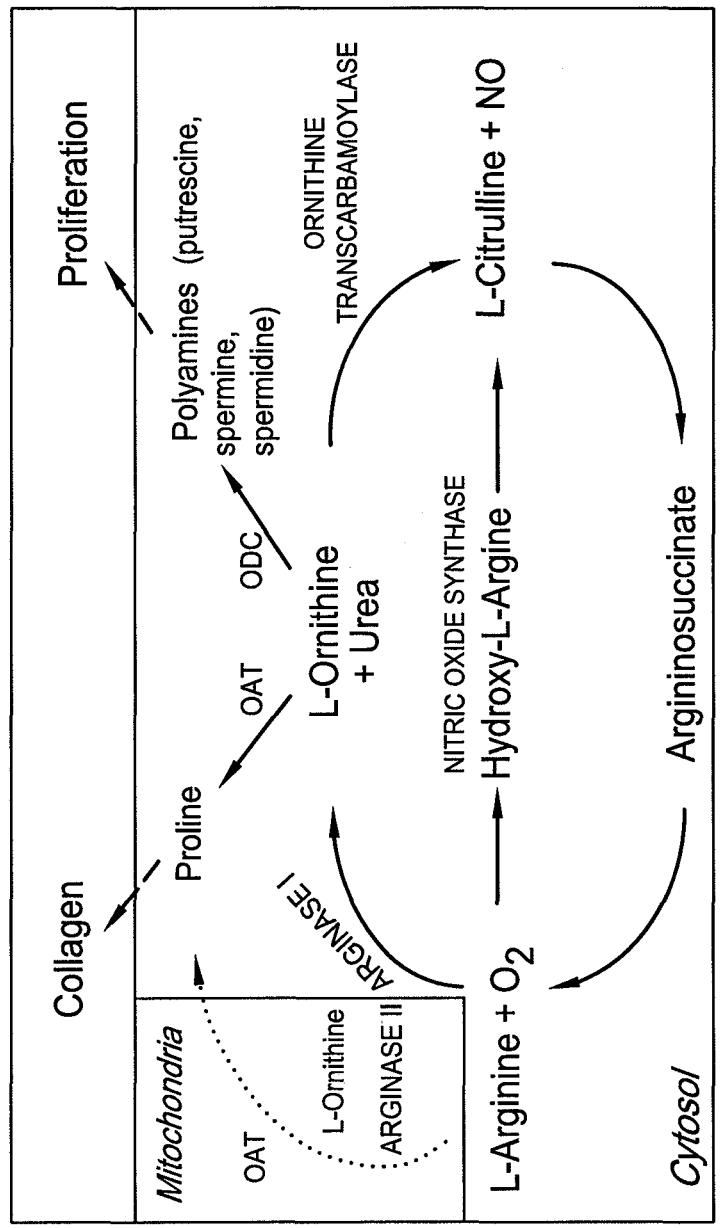

COMPOSITIONS COMPRISING DIMETHYL SULFOXIDE (DMSO)

RELATED APPLICATIONS

This application is the U.S. National Phase under 35 U.S.C. §371 of International Application No. PCT/US2006/035320, filed Sep. 11, 2006 (published as WO 2007/033082A1), which claims priority to U.S. Provisional Patent Application Ser. No. 60/716,335, filed Sep. 12, 2005, all herein incorporated by reference.

BACKGROUND OF THE INVENTION

1. Field of the Invention

The present invention relates generally to pharmaceutical compositions and medicaments comprising dimethyl sulfoxide (DMSO) and/or related compounds in combination with one or more other compounds, such as L-arginine, fructose 1,6-diphosphate, L-lysine, L-aspartate, and urea.

2. Description of the Related Art

Traumatic brain injury and stroke generally cause a reduction in cerebral blood flow (CBF), which may cause additional damage to the brain. Applicant believes that there are presently no known therapeutic agents which increase CBF in a sustained fashion (for at least several days) after traumatic brain injury. (Narayan K, and NIH Collaborative Committee. Clinical trials in head injury. J. Neurotrauma. 2002; 19(5):503-57, herein incorporated by reference).

Nitric oxide (NO) is a multifunctional messenger molecule that has a prominent role in the regulation of CBF and cell-to-cell communication in the brain. Its highest levels in the body is found in neurons. NO is synthesized from L-arginine by a family of enzymes called NO synthases (NOS). Release of NO from cerebral endothelial cells to produce vasodilation is a fairly well established reaction. NO has been shown to diffuse towards the lumen of blood vessels in humans where it helps maintain blood fluidity, and by inference, reduce blood viscosity, thus improving blood flow. (Moncada, S., Palmer, R. M., and Higgs, E. A. Nitric oxide: physiology, pathophysiology, and pharmacology. Pharmacol. Rev 1991; 43, 109-142; Ignarro L, Napoli C. Novel features of nitric oxide, endothelial nitric oxide synthase, and atherosclerosis. Curr Atheroscler Rep. 2004 July; 6(4):281-7, herein incorporated by reference).

Arginine is a basic amino acid that plays several pivotal roles in cellular physiology. Like any amino acid, it is involved with protein synthesis, but it is also intimately involved with cell signaling through the production of NO and cell proliferation through its metabolism to ornithine and the other polyamines. Because of these multiple functions, arginine is an essential substrate for healing processes involving tissue trauma. Numerous studies have shown that arginine supplementation can lead to normalization or improvement of wound healing. (Barbul A. Arginine: biochemistry, physiology, and therapeutic implications. J Parent Enteral Nutr 1986; 10:227-238; Cheman L. L-Arginine and Free Radical Scavengers Increase Cerebral Blood Flow and Brain Tissue Nitric Oxide Concentrations after Controlled Cortical Impact Injury in Rats. Journal of Neurotrauma, January 2003, 20 (1): 77-85; Hlatky R. The Role of Endothelial Nitric Oxide Synthase in the Cerebral Hemodynamics after Controlled Cortical Impact Injury in Mice. Journal of Neurotrauma, 2003, 20 (10): 995-1006, all herein incorporated by reference).

Studies have shown that L-arginine administration after experimental traumatic injury in mice increased CBF post-injury. L-Arginine administration also resulted in a reduction in contusion volume in the L-arginine treated mice. The likely explanation for these results is that the increase in CBF was beneficial to the outcome of the head injury in these animals, and such action is mediated by vascular NO. These findings suggest an important role for vascular NO produced by endothelial NO synthase (eNOS) in the preservation of cerebral blood flow in contused brain following traumatic injury, and in the improvement in cerebral blood flow with L-arginine administration. Normal synthesis of vascular NO from L-arginine is achieved by the action of eNOS and specific co-factors nicotinamide adenine dinucleotide phosphate (NADPH) and tetrahydrobiopterin ($BH_4$) in the endothelium.

L-arginine is a non-toxic, inexpensive, natural amino acid that can be given in high doses orally for prolonged periods of several months or intravenously for several weeks. (Piatti P, Fragasso G, Monti L D, Setola E, Lucotti P, Fermo I, Paroni R, Galluccio E, Pozza G, Chierchia S, Margonato A. Acute intravenous L-arginine infusion decreases endothelin-1 levels and improves endothelial function in patients with angina pectoris and normal coronary arteriograms: correlation with asymmetric dimethylarginine levels. Circulation. 2003; 107(3):429-36, herein incorporated by reference).

Arginine is a dibasic amino acid, and is found in many proteins in the body. Its metabolism is intimately tied to several metabolic pathways involved in the synthesis of urea, NO, polyamines, agmatine, and creatine phosphate. (FIG. 1). Arginine can be provided via nutritional intake, via new synthesis, or via systemic administration, for example, intravenously. About 50% of the ingested arginine is released into the portal circulation. The other part is directly utilized in the small bowel. The physiological uptake of arginine and citrulline by the liver is low because the liver does not express large amounts of the cationic transporter for the basic amino acid arginine. Therefore, most of the portal venous arginine and citrulline enters the systemic circulation and serves as substrate for extrahepatic tissues. The kidney metabolizes citrulline into arginine (the "intestinal-renal axis") and exports arginine into the systemic circulation. (FIG. 1).

The average nutritional arginine uptake is approximately 5-6 g/day. Standard rodent laboratory chow diets contain about 1% L-arginine, which corresponds to an average intake of 1 g arginine/kg body weight/day. Arginine-deficient rats subjected to minor trauma lose significantly more weight and are more likely to experience mortality when compared to arginine-repleted animals.

Arginine catabolism occurs via several enzymatic pathways (FIG. 1). The two major catabolic pathways during healing after trauma are degradation via NO synthase (NOS) isoforms and via the two arginase isoforms. Both pathways deplete extracellular arginine concentrations in the wound milieu, thus rendering arginine an essential amino acid for wound healing. The current interest in L-arginine is due mainly to its close relation with the important signal molecule NO.

The major isoform of NOS activation during healing after trauma is inducible nitric oxide synthase (iNOS), which generates larger amounts of NO than the constitutive isoforms (endothelial NOS and neuronal NOS). Major sources of iNOS are macrophages but also fibroblasts, endothelial cells, and keratinocytes. Strong counter-regulating mechanisms exist between the two catabolic pathways. Intermediates and end products of each pathway can reciprocally inhibit each other. Each pathway is stimulated by a well-defined set of cytokines that in turn also down-regulates the alternate pathway.

Arginase exists in two different isoforms. Arginase I is the cytosolic "hepatic" isoform that is also present in wound-derived fibroblasts. Arginase II, the mitochondrial extrahepatic isoform, is present in many other cell types such as macrophages, kidney, breast tissue, and enterocytes. The two isoforms are encoded by different genes and have their own distinct regulation. It is unclear which isoform, if any, plays the predominant role in the wound environment.

The main source of vascular NO in mammals is derived from eNOS contained within the endothelial cells. The loss or uncoupling of eNOS impairs cerebrovascular function in part by promoting vasoconstriction, platelet aggregation, smooth muscle cell proliferation, leukocyte adhesion and greater endothelial-immune cell interaction. Vascular NO production from the endothelium is regulated by eNOS enzyme activity and/or NOS gene expression. (Kubes P. and Granger, D. N. (1992). Nitric oxide modulates microvascular permeability. Am. J. Physiol. 262, H611-H615, herein incorporated by reference).

Besides the key role vascular NO plays in vascular tone, blood pressure and vascular homeostasis, it also acts to inhibit platelet and leukocyte adhesion to the endothelium, a process that may down-regulate pro-inflammatory events. (Kubes P., Kanwar S., Niu X. F. (1993). Nitric oxide synthesis inhibition induces leukocyte adhesion via superoxide and mast cells. FASEB J. 7, 1293-1299, herein incorporated by reference).

When trauma to the brain reduces cerebral blood flow (CBF), formation of reactive oxygen species (ROS) at the injury site may induce a deficiency in tetrahydrobiopterin ($BH_4$), a rate limiting step in eNOS synthesis, resulting in eNOS uncoupling and reduced release of vascular NO. Reduced vascular NO is reported to involve many changes including: endothelial cell (EC) shape changes, mitochondrial stress, reduced eNOS, impaired glucose transporter 1 (thus lowering glucose delivery to brain cells), tumor necrosis factor-alpha (TNF-alpha) activation, neutral factor-kappa B (NF-kB) translocation from cytosol to nucleus and activation of transcription inflammatory genes, release of the powerful vasoconstrictor endothelin-1 (ET-1), migration of vascular smooth muscle cells (VSMC) leading to the formation of vessel wall plaques, activation of hypoxic inducible factor-1alpha (HIF-1alpha), increase of vascular adhesion molecules (VCAM), increased beta peptide angiopathy, excess free radical formation including hydrogen peroxide ($H_2O_2$) and superoxide anion ($SO^-$), impairment of the angiogenic vascular endothelial growth factor (VEGF) and persistent shear-stress on vessel walls. (de la Torre J C, Stefano G B. Evidence that Alzheimer's disease is a microvascular disorder: Role of constitutive nitric oxide. Brain Res Rev. 34:119-136, 2000, herein incorporated by reference).

Vascular NO therefore, acts as an antiatherogenic, antithrombotic and anti-ischemic molecule. No does this by reducing oxidative stress, by preventing platelet aggregation and by stimulating angiogenesis via vascular endothelial growth factor (VEGF) while reducing shear stress on the vessel wall.

The increased synthesis of vascular NO by L-arginine appears to be a logical approach for the treatment of severe traumatic brain injury, acute ischemic stroke, and neurodegenerative disorders such as Alzheimer's disease, Parkinson's disease, subacute sclerosing panencephalitis, vascular dementia, multiple sclerosis, assorted neuropathies, Huntington's disease, amyotrophic lateral sclerosis (ALS) and leukodystrophies.

L-arginine produces peak plasma levels approximately 1-2 hours after oral administration. The most common adverse reactions of higher doses, from 15 to 30 grams daily, are nausea, abdominal cramps and diarrhea. (Visser J J, Hoekman K. Arginine supplementation in the prevention and treatment of osteoporosis. Med. Hypotheses. 1994 November; 43(5):339-42, herein incorporated by reference).

Additionally, L-arginine given as a continuous intravenous infusion for 120 minutes at a rate of 0.125 g/min, for angina pectoris, was able to reduce the levels of endothelin-1, one of the most powerful vasoconstrictors known and also lowered the serum levels of asymmetric dimethylarginine (ADMA), an endogenous inhibitor of eNOS.

DMSO has been shown to increase CBF in a variety of brain injuries including stroke and head trauma in animals and humans. The combination of DMSO with fructose 1,6-diphosphate has been reported to of benefit to victims of acute and chronic human stroke. The mechanism of DMSO action for increasing CBF after brain injury is not clear but may be due to its ability to: i) reduce cerebrovascular reactivity, ii) deaggregate platelets in blood vessels thus augmenting blood fluidity by decreasing blood viscosity and iii) reducing intracranial pressure, thus allowing compressed blood vessels in brain tissue to return to a more normal hemodynamic state. DMSO is not known to affect vascular nitric oxide, ADMA or endothelin-1. (de la Torre, J. C. and Surgeon, J. W.: Dexamethasone and DMSO in cerebral infarction. Stroke, 7:577-583, 1976; de la Torre, J. C., Kawanaga, H. M., Goode, D. J., Johnson, C. M., Kajihara, K., Rowed, D. W. Mullan, S.: Dimethyl sulfoxide in CNS trauma. Ann. N.Y. Acad. Sci., 243:362-389, 1975; Brown F D, Johns L M, Mullan S. Dimethyl sulfoxide in experimental brain injury, with comparison to mannitol. J. Neurosurg. 1980 July; 53(1):58-62; Karaca M, Kilic E, Yazici B, Demir S, de la Tone J C. Ischemic stroke in elderly patients treated with a free radical scavenger-glycolytic intermediate compound. Neurol Res, 24:73-80, 2002; Karaca, M., Bilgin, U., Akar, M. and de la Torre, J. C.: Dimethyl sulfoxide lowers ICP after closed head trauma. Eur. J. Clin. Pharmacol., 40:113-114, 1991, all herein incorporated by reference).

Ischemia has been proposed to cause an excess increase in the extracellular concentration of glutamate, an excitotoxic amino acid, in the central nervous system. (Benveniste H, Drejer J, Schousboe A, Diemer N H: Elevation of the extracellular concentrations of glutamate and aspartate in rat hippocampus during transient cerebral ischemia monitored by intracerebral microdialysis. J Neurochem 1984; 43: 1369-74, herein incorporated by reference).

The increased glutamate in turn triggers a surplus influx of calcium ion (Ca2+) from the extracellular space into the cytosol, resulting in the initiation of a neuronal cell death cascade. The extracellular glutamate concentration is tightly regulated by release from presynaptic membranes and uptake by postsynaptic membranes and glia. This regulation is closely linked to alterations in intracellular free calcium concentration; namely, an increase in intracellular Ca2+ may enhance glutamate release from glutamatergic neurons and astrocytes. Therefore, controlling the extracellular glutamate and intracellular Ca2+ concentrations could be a promising strategy for alleviating ischemic and traumatic neuronal damage. (Kristian T, Siesjö; B K: Calcium in ischemic cell death. Stroke 1998; 29: 705-18; Rossi D J, Oshima T, Attwell D: Glutamate release in severe brain ischaemia is mainly by reversed uptake. Nature 2000; 403: 316-21; Bezzi P, Carmignoto G, Pasti L, Vesce S, Rossi D, Rizzini B L, Pozzan T, Volterra A: Prostaglandins stimulate calcium-dependent glutamate release in astrocytes. Nature 1998; 391: 281-292, all herein incorporated by reference).

It has been reported that concentrations of DMSO to which neurons are typically exposed in experimental studies and in human patients (0.5-1.5%) inhibit glutamate responses in hippocampal neurons. DMSO suppresses, in a rapidly reversible manner, electrophysiological responses and calcium influx induced by glutamate, NMDA (N-methyl-1-aspartate), and AMPA (α-amino-3-hydroxy-5-methylisoxazole-4-propionate). Moreover, DMSO can prevent excitotoxic death of the neurons induced by glutamate. The findings have important implications for the use of DMSO as a therapeutic agent that involve glutamatergic excitotoxicity after head trauma. These findings by an NIH group of investigators identify a mechanism that might explain the beneficial clinical effects of DMSO on CNS neurons and suggest a potential use for DMSO in the treatment of excitotoxic traumatic and neurodegenerative conditions. (Lu, C., and M. P. Mattson. 2001 July. Dimethyl sulfoxide suppresses NMDA- and AMPA-induced ion currents and calcium influx and protects against excitotoxic death in hippocampal neurons. Exp Neurol 170:180-185; Marshall L F, Camp P, Bowers S. Dimethyl sulfoxide for the treatment of intracranial hypertension. J Neurosurg 1984; 14: 659-663, herein incorporated by reference).

SUMMARY OF THE INVENTION

In one embodiment, the invention comprises the use of a composition comprising dimethylsulfoxide (DMSO) in the preparation of a medication for the treatment of stroke or brain injury, wherein said composition additionally comprises one or more of the following: L-arginine and urea. About 1.0 to 8.0 grains of L-arginine may be dissolved in a DMSO solution. DMSO may be provided in a concentration of about 20% to about 40%. In one embodiment, a dose of 70 grams of DMSO is used. About 20% to about 60% urea can be used. In one embodiment, a combination (e.g., a solution) of about 50% DMSO and 50% urea is provided. Brain injuries may include spinal cord injuries. Brain injuries may be degenerative disorder, as a result of trauma, or both.

In one embodiment, DMSO is provided to lower intracranial pressure and increase cerebral blood flow, thereby providing an effective brain injury treatment. Arginine can also increase cerebral blood flow, perhaps by forming nitric oxide. Together, DMSO and arginine may have a combined, additive, or synergistic effect. In some embodiments, DMSO and arginine (or NO) act on different receptors or pathways to increase blood flow more than either of the compounds administered alone. In other embodiments, DMSO and arginine (or NO) act on the same receptors or pathways to increase blood flow.

In several of the embodiments described herein, one or more DMSO associated compounds, such as methylsulfonylmethane (MSM or $DMSO_2$) and dimethyl sulfide or methylthiomethane (DMS), are provided in addition to or instead of DMSO. For example, in one embodiment, a composition comprising DMS and L-arginine is provided. In other embodiments, DMS and L-arginine are provided along with one or more of the following: fructose 1,6-diphosphate, L-lysine, L-aspartate, urea, DMSO, MSM, and other DMSO metabolites.

Because arginine is the immediate precursor of NO, urea, ornithine and agmatine, in some embodiments, NO, urea, ornithine and agmatine are used in addition to or instead of L-arginine in several of the compositions described herein. Because arginine is synthesized from citrulline, citrulline may be used in addition to or instead of L-arginine in several of the compositions described herein. Other forms of arginine, other than the L isomer may also be used. The compositions described herein may comprise nitric oxide synthase to facilitate the production of NO from arginine.

As discussed above, L-arginine given as a continuous intravenous infusion was able to reduce the levels of endothelin-1, one of the most powerful vasoconstrictors known and also lowered the serum levels of asymmetric dimethylarginine (ADMA), an endogenous inhibitor of eNOS. L-arginine combined with L-aspartate or L-lysine can increase its peak levels in physiological conditions such as an increase in growth hormones and bone metabolism. It is therefore anticipated that the addition of L-lysine and/or L-aspartate to L-arginine should increase the efficacy of this amino acid in traumatic or degenerative brain conditions, according to several embodiments of the invention.

In one embodiment, the present invention comprises a composition comprising DMSO and L-arginine, DMSO and urea, or DMSO, L-arginine, and urea. In other embodiments, the present invention comprises a composition comprising DMSO, L-arginine, and additional compound selected from the group consisting of one or more of the following: fructose 1,6-diphosphate, L-lysine, L-aspartate, and urea. In one embodiment, a synergistic effect is obtained when DMSO and L-arginine are combined with these additional compounds.

In another embodiment, the invention comprises a DMSO solution and one or more of the following: L-arginine, fructose 1,6-diphosphate, L-lysine, L-aspartate, and urea. In one embodiment, a synergistic effect is obtained when DMSO is combined with these additional compounds. In one embodiment, about 200 to 900 mg of L-lysine is dissolved in (or otherwise combined with) the DMSO solution. In another embodiment, about 100 to 1,200 mg of the L-aspartate is dissolved in (or otherwise combined with) the DMSO solution.

In yet another embodiment, the invention comprises a pharmaceutical composition according to any of the embodiments described herein that is provided to a patient to treat brain injuries, atherosclerosis, stroke, or neurodegenerative disorders.

In one embodiment, the present invention comprises a method of treating brain injury or stroke, comprising administering a therapeutically effective dose of a composition according to any one of the preceding claims to an individual in need thereof.

In one embodiment, the invention comprises a pharmaceutical composition according to any of the embodiments described herein that is provided to a patient as a neuroprotectant.

In another embodiment, the pharmaceutical composition is provided orally and/or intravenously to a patient to prevent or treat a pathologic condition.

The pharmaceutical compositions described above may be provided intravenously to a patient to prevent or treat a pathologic condition. In one embodiment, the intravenous solution is provided at a rate of about 10 ml/min.

In one embodiment, the invention comprises the use of a composition comprising in the preparation of a medication for the treatment of stroke or brain injury, wherein said composition additionally comprises one or more of the following: L-arginine and urea. DMS may be provided in a concentration of about 5% to about 50%.

In yet another embodiment, a preventative or therapeutic method of increasing cerebral blood flow is provided. In one embodiment, the method comprises administering to an individual dimethylsulfoxide (DMSO) and one or more of the following: L-arginine and urea.

BRIEF DESCRIPTION OF THE DRAWING

FIG. 1 is a schematic diagram showing L-arginine metabolic pathways.

DETAILED DESCRIPTION OF THE PREFERRED EMBODIMENTS

In several embodiments, the present invention provides compositions, pharmaceutical compositions and medicaments comprising DMSO and/or a DMSO associated compound (such as DMS) combined with one or more of the following: L-arginine, L-fructose 1,6-diphosphate, L-lysine, L-aspartate, urea or a metabolite or derivative thereof. The invention also provides methods of using these compositions for treatments of various disorders. In a preferred embodiment, the composition comprises DMSO and L-arginine. In another embodiment, the composition comprises one or more DMSO metabolites or derivatives thereof and L-arginine.

The phrases "DMSO associated compounds", "associated compounds", or "related compounds" as used herein shall be given their ordinary meaning and shall include degradation compounds, derivatives, precursors, and metabolites of DMSO, such as methylsulfonylmethane (MSM or $DMSO_2$) and dimethyl sulfide or methylthiomethane (DMS). Metabolites include compounds to which DMSO is converted within the cells of a mammal. For example, the pharmaceutical compositions of several embodiments of the present invention may include a metabolite of DMSO instead of DMSO. The scope of the methods of several embodiments of the present invention includes those instances where DMSO is administered to the patient, yet the metabolite is the bioactive entity.

The terms "pharmaceutical composition" or "formulation" as used herein shall be given their ordinary meaning, be used interchangeably, and shall include a mixture of the components listed herein, or a pharmaceutically acceptable salt, prodrug, ester or amide thereof, with other chemical components, such as diluents or carriers. The pharmaceutical composition may facilitate administration of the compound to an organism. Multiple techniques of administering a compound exist in the art including, but not limited to, oral, rectal, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" as used herein shall be given its ordinary meaning and shall include a compound that facilitates the incorporation of a compound into cells or tissues.

The term "treating" or "treatment" does not necessarily mean total cure. Any alleviation, amelioration, prevention, or reversal any undesired signs or symptoms of the disease to any extent or the slowing down of the progress of the disease can be considered treatment. Furthermore, treatment may include acts that may worsen the patient's overall feeling of well being or appearance. Treatment may also include lengthening the life of the patient, even if the symptoms are not alleviated, the disease conditions are not ameliorated, or the patient's overall feeling of well being is not improved.

In one embodiment, the invention provides a combination of DMSO (about 1 gram in a 28% solution) and L-arginine (about 1.0 to 8.0 g dissolved in the DMSO solution). In other embodiments, about 10 grams to about 200 grams, preferably about 40 grams to 100 grams, and more preferably about 70 grams of DMSO is administered to an individual in a dose. In several embodiments, a concentration of about 5% to about 50%, preferably about 15% to about 40%, and more preferably about 30% DMSO in solution (such as dextrose, water or physiological saline) is provided in a dose. Doses may be administered daily, weekly, monthly, or as needed. Other time intervals for dosing may also be appropriate.

In one embodiment, the composition is provided as a pharmaceutical formulation which is used to treat a patient with brain injury or stroke. In one embodiment, the pharmaceutical formulation is provided intravenously at a rate of about 1 ml/min to about 30 ml/min, or preferably about 10 ml/min administered. Administration at a rate less than 1 ml/min or greater than 30 ml/min can also be used. Other pathologies may also benefit from this combination, including traumatic brain injury, ischemic stroke, atherosclerosis, neurodegeneration, and spinal cord trauma.

In one embodiment, the invention provides a pharmaceutical formulation comprising DMSO, L-arginine, and L-lysine. In one embodiment, the invention comprises a pharmaceutical formulation comprising DMSO and L-lysine. In another embodiment, one or more additional amino acids are included.

In one embodiment, the combination of DMSO, L-arginine (about 1.0 to 8.0 g dissolved in the DMSO solution), and L-lysine (about 200 to 900 mg dissolved in the DMSO solution) is provided. In one embodiment, the combination is provided intravenously a rate of about 10 ml/min and is administered for traumatic brain injury or for stroke. In some embodiments, DMSO is provided in a concentration of about 20%-40%.

In one embodiment, the invention comprises a pharmaceutical composition comprising DMSO and L-aspartate. In one embodiment, the invention comprises a pharmaceutical composition comprising DMSO, L-arginine, and L-aspartate. In some embodiments, DMSO is provided in a concentration of about 20%-40%.

In one embodiment, a combination of DMSO, L-arginine (about 1.0 to 8.0 g dissolved in the DMSO solution), and L-aspartate (about 100 to 1,200 mg dissolved in the DMSO solution) is given intravenously at a rate of 10 ml/min and administered for traumatic brain injury or for stroke In some embodiments, DMSO is provided in a concentration of about 20%-40%.

The safety of intravenous DMSO is well-established. L-arginine has been shown in numerous studies to be safe at doses up to 30 grams/day, or intravenously at doses up to 15 g/day. The typical dietary intake of L-arginine is 3.5 to 5 grams daily. This semi-essential amino acid has not been used extensively for intravenous administration and its use is mainly through the oral route. L-aspartate and L-lysine have been given in doses of 250 mg/Kg without adverse effects. All of these compounds are commercially available.

Supplemental L-arginine may have anti-atherogenic, antioxidant and immunomodulatory actions. It may also have wound-repair activity. Thus, in one embodiment, L-arginine is administered in combination with DMSO (or DMSO metabolites or derivatives) to treat pathologies in which anti-atherogenic, antioxidant, immunomodulatory actions, and/or wound-repair activity would be desirable. Such pathologies include atherosclerosis, cancer, systemic lupus erythematosus, arthritis, inflammation, and autoimmune disease.

In one embodiment, the invention comprises a combination of DMSO, L-arginine, and one or more of the following: fructose 1,6-diphosphate, L-lysine, L-aspartate, and urea. In another embodiment, DMSO and urea is used together or in combination with L-arginine, fructose 1,6-diphosphate, L-lysine, L-aspartate. A DMSO associated compound may be used in addition to, or instead of DMSO, in any of the embodiments described herein.

The compositions and combinations described herein may be used to prevent or treat one or more of the following pathologies: traumatic brain injury, ischemic stroke, atherosclerosis, spinal cord trauma, and other dementias, and as a neuronal protector to prevent brain damage, for example, during coronary artery bypass graft (CABG). These compositions may also be used to treat neurodegenerative disorders including, but not limited to, Alzheimer's disease, Parkinson's disease, subacute sclerosing panencephalitis, vascular dementia, multiple sclerosis, assorted neuropathies, Huntington's disease, amyotrophic lateral sclerosis (ALS) and leukodystrophies.

The amounts of L-arginine, fructose 1,6 diphosphate and L-aspartate to be combined with the DMSO will vary depending of the disorder to be treated, severity of the disorder and age of the patient, but in general the amounts of these compounds will range from about 0.5% w/v to about 10% w/v.

Several embodiments of the present invention is also directed to the use of any of the DMSO-containing compositions described hereinabove for treatment of any of the disorders disclosed herein. In addition, other embodiments are directed to the use of any of the DMSO-containing compositions described above in the preparation of a medicament for treatment of any of the disorders described herein.

The pharmaceutical compositions described herein can be administered to a human or non-human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, topical, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly in the renal or cardiac area, often in a depot or sustained release formulation. Furthermore, one may administer the drug in a targeted drug delivery system, for example, in a liposome coated with a tissue-specific antibody. The liposomes will be targeted to and taken up selectively by the organ.

The pharmaceutical compositions according to several embodiments of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with several embodiments of the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For injection, the agents according to several embodiments of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

For topical administration, the compounds may be formulated for administration to the epidermis as ointments, gels, creams, pastes, salves, or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally, including sublingually, which include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to several embodiments of the present invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-fi-ee water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds used in the pharmaceutical combinations of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

Pharmaceutical compositions suitable for use in several embodiments of the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions according to several embodiments of the present invention can be chosen by the individual physician in view of the patient's condition. (See e.g., Fingl et al 1975, in "The Pharmacological Basis of Therapeutics", Ch. 1 p. 1). Typically, the dose range of the composition administered to the patient can be from about 0.5 to 1000 mg/kg of the patient's body weight. The dosage may be a single one or a series of two or more given in the course of one or more days, as is needed by the patient. A suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between 0.1 mg and 6000 mg of each ingredient, preferably between 1 mg and 5000 mg, e.g. 25 to 5000 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions of the present invention or a pharmaceutically acceptable salt thereof calculated as the free base, the composition being administered 1 to 4 times per day. Alternatively the compositions of the invention may be administered by continuous intravenous infusion, preferably at a dose of each ingredient up to 400 mg per day.

Thus, the total daily dosage by oral administration of each ingredient will typically be in the range 1 to 2500 mg and the total daily dosage by parenteral administration will typically be in the range 0.1 to 400 mg. Suitably the compounds will be administered for a period of continuous therapy, for example for several days, a week or more, or for months or years. DMSO alone or in combination with the compounds described herein may be administered as a one-time therapy immediately upon affliction of injury. A low dose of DMSO alone or in combination with the compounds described may be administered on a regular basis to individuals susceptible to stroke, and thereby serve as a preventative measure or as a measure that would lower the risk of having a stroke or other illnesses that are related to cerebral blood flow.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen that maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

What is claimed is:

1. A method of treating brain injury, the method consisting essentially of:
    administering a composition consisting essentially of dimethylsulfoxide (DMSO), L-arginine and one or more pharmaceutically-acceptable carriers to a brain injury patient,
    wherein the DMSO is present in a concentration range of about 20% to about 40% in the composition,
    wherein the L-arginine is present in a range of about 0.5% to about 10% weight per volume of the composition,
    wherein the administering is intravenous, and
    wherein the brain injury is a spinal cord injury or a traumatic brain injury.

2. The method of claim 1, further comprising preparing the composition prior to the administering, wherein the preparing comprises combining at least the DMSO and the L-arginine.

3. The method of claim 1, wherein the DMSO is present in the composition in has a concentration in a range of about 20% to about 30%.

4. The method of claim 1, wherein the DMSO is present in in the composition in a concentration of about 28%.

5. The method of claim 1, wherein the pharmaceutically-acceptable carrier is saline.

6. A method of treating a patient with brain injury, said method comprising:
    obtaining a composition comprising dimethylsulfide (DMS) and L-arginine in a therapeutically effective dose,
    wherein said therapeutically effectively dose of DMS is a concentration of about 20% to 40% of said composition and said therapeutically effective dose of L-arginine is about 0.5% to about 10% weight per volume of said composition; and
    administering said composition intravenously to said patient, wherein said brain injury is a spinal cord injury or a traumatic brain injury.

7. The method of claim 6, further comprising administering at least one of methylsulfonylmethane (MSM), urea, and dimethylsuloxide (DMSO).

8. The method of claim 7, wherein the administering at least one of methylsulfonylmethane (MSM), urea, and dimethylsulfoxide (DMSO) comprises administering orally.

9. The method of claim 6, wherein the dimethylsulfide (DMS) is present in said composition in a concentration of about 28%.

10. The method of claim 6, wherein said composition further comprises a compound selected from the group consisting of one or more of the following: L-lysine and L-aspartine.

11. The method of claim 6, wherein said composition further comprises urea in a concentration in a range of about 20% to about 60%.

12. The method of claim 11, wherein at least one of said DMSO, said L-arginine, and said urea is administered intravenously at a rate of about 10 ml/min.

13. A method of increasing blood flow in the central nervous system, consisting essentially of:
    intravenously administering a therapeutically effective dose of a pharmaceutical composition consisting essentially of dimethylsulfoxide (DMSO), L-arginine, and one or more pharmaceutically-acceptable carriers to a subject having a spinal cord injury or a traumatic brain injury.

14. A method of treating brain injury, consisting essentially of:
    administering a therapeutically effective dose of a pharmaceutical composition consisting essentially of dimethylsulfoxide (DMSO), L-arginine, urea, and one or more pharmaceutically-acceptable carriers
    to an individual having a brain injury, wherein said brain injury comprises a spinal cord injury or a traumatic brain injury.

15. A method of treating brain injury, the method consisting essentially of:
    administering a composition consisting essentially of DMSO, L-arginine and one or more pharmaceutically-acceptable carriers to a brain injury patient,
    wherein said DMSO is present in a concentration range of about 20% to about 40% in the first composition, wherein said L-arginine is present in a range of about 0.5% to about 10% weight per volume of said first composition, wherein said brain injury is a spinal cord injury or a traumatic brain injury.

16. A method of treating brain injury, consisting essentially of:

administering a therapeutically effective dose of a pharmaceutical composition consisting essentially of dimethylsulfoxide (DMSO), L-arginine, MSM, and one or more pharmaceutically-acceptable carriers to an individual having a brain injury, wherein said brain injury comprises a spinal cord injury or a traumatic brain injury.

17. A method of treating brain injury, comprising:

administering a therapeutically effective dose of a composition comprising dimethylsulfide (DMS), L-arginine, MSM, and one or more pharmaceutically-acceptable carriers to an individual having a brain injury, wherein said brain in jury comprises a spinal cord injury or a traumatic brain injury.

18. A method of treating brain injury, comprising:

administering a therapeutically effective dose of a pharmaceutical composition comprising dimethylsulfide (DMS), L-arginine, urea, and one or more pharmaceutically-acceptable carriers to an individual having a brain injury, wherein said brain injury comprises a spinal cord injury or a traumatic brain injury.

19. A method, comprising:

administering a composition to a patient, the composition consisting essentially of:

dimethylsulfoxide (DMSO), at least one of L-arginine, L-lysine, L-aspartate, dimethylsulfide (DMS), methylsulfonylmethane (MSM), and urea, and one or more pharmaceutically-acceptable carriers.

20. The method of claim 19, wherein the patient is a brain injury patient.

21. The method of claim 20, wherein the brain injury is a spinal cord injury or a traumatic brain injury.

22. A method, comprising:

administering a composition to a patient, the composition comprising:

dimethylsulfide (DMS), at least one of L-arginine, L-lysine, L-aspartate, dimethylsulfoxide (DMSO), methylsulfonylmethane (MSM), and urea, and one or more pharmaceutically-acceptable carriers.

23. The method of claim 22, wherein the patient is a brain injury patient.

24. The method of claim 23, wherein the brain injury is a spinal cord injury or a traumatic brain injury.

* * * * *